US009336283B2

(12) United States Patent
Giang et al.

(10) Patent No.: US 9,336,283 B2
(45) Date of Patent: May 10, 2016

(54) SYSTEM AND METHOD FOR DATA SENSITIVE FILTERING OF PATIENT DEMOGRAPHIC RECORD QUERIES

(75) Inventors: Phan H. Giang, Downingtown, PA (US); William A. Landi, Devon, PA (US); Sathyakama Sandilya, London (GB)

(73) Assignee: Cerner Innovation, Inc., Kansas City, KS (US)

(*) Notice: Subject to any disclaimer, the term of this patent is extended or adjusted under 35 U.S.C. 154(b) by 709 days.

(21) Appl. No.: 11/443,862

(22) Filed: May 31, 2006

(65) Prior Publication Data
US 2006/0294092 A1 Dec. 28, 2006

Related U.S. Application Data

(60) Provisional application No. 60/686,065, filed on May 31, 2005.

(51) Int. Cl.
G06F 17/30 (2006.01)
G06F 19/00 (2011.01)

(52) U.S. Cl.
CPC .... G06F 17/30533 (2013.01); G06F 17/30389 (2013.01); G06F 17/30536 (2013.01); G06F 19/322 (2013.01)

(58) Field of Classification Search
CPC ................ G06F 17/30536; G06F 17/30533
USPC ................... 707/1, 3, 6, 5; 382/173
See application file for complete search history.

(56) References Cited

U.S. PATENT DOCUMENTS

| 5,084,815 A | 1/1992 | Mazzario |
| 5,497,486 A | 3/1996 | Stolfo et al. |
| 5,506,984 A | 4/1996 | Miller |

(Continued)

FOREIGN PATENT DOCUMENTS

| EP | 1 077 415 | 2/2001 |
| JP | 10320420 A | 12/1998 |

(Continued)

OTHER PUBLICATIONS

Murphy et al., "The Ranked Probability Score and The Probability Score: A Comparison", Feb. 16, 1970.*

(Continued)

*Primary Examiner* — Mariela Reyes
*Assistant Examiner* — Dawaune Conyers
(74) *Attorney, Agent, or Firm* — Shook, Hardy & Bacon L.L.P.

(57) ABSTRACT

A method for data sensitive filtering in a patient database searches includes providing a search criteria comprising one or more search locator fields, determining a retrieval formula from the search criteria that maximizes error tolerance in the search criteria while satisfying a predefined response time requirement, and retrieving candidate records from the database. If no retrieval formula can be found that satisfies the response time requirements, the method includes requesting additional search criteria, scoring each candidate record by comparing a search criteria locator field with a corresponding retrieved record field, and determining whether the score of the candidate record exceeds a predefined threshold. If the candidate score does exceed the threshold, the candidate record is added to a list of records to be returned in response to the search criteria.

21 Claims, 5 Drawing Sheets

(56) References Cited

U.S. PATENT DOCUMENTS

| | | | |
|---|---|---|---|
| 5,544,044 | A | 8/1996 | Leatherman |
| 5,560,005 | A | 9/1996 | Hoover et al. |
| 5,664,109 | A | 9/1997 | Johnson et al. |
| 5,680,611 | A | 10/1997 | Rail et al. |
| 5,717,915 | A | 2/1998 | Stolfo et al. |
| 5,724,575 | A | 3/1998 | Hoover et al. |
| 5,724,597 | A * | 3/1998 | Cuthbertson et al. ......... 715/201 |
| 5,724,968 | A | 3/1998 | Lliff |
| 5,737,539 | A | 4/1998 | Edelson et al. |
| 5,806,061 | A | 9/1998 | Chaudhuri et al. |
| 5,895,461 | A | 4/1999 | De La Huerga et al. |
| 5,899,998 | A | 5/1999 | McGauley et al. |
| 5,903,889 | A | 5/1999 | de la Huerga et al. |
| 5,907,839 | A | 5/1999 | Roth |
| 5,970,497 | A | 10/1999 | Burrows |
| 6,018,735 | A * | 1/2000 | Hunter .............................. 707/5 |
| 6,061,503 | A | 5/2000 | Chamberlain |
| 6,119,126 | A | 9/2000 | Yee et al. |
| 6,151,604 | A | 11/2000 | Wlaschin et al. |
| 6,168,568 | B1 | 1/2001 | Gavriely |
| 6,230,158 | B1 | 5/2001 | Burrows |
| 6,240,417 | B1 | 5/2001 | Eastwick et al. |
| 6,266,675 | B1 | 7/2001 | Evans et al. |
| 6,295,541 | B1 | 9/2001 | Bodnar et al. |
| 6,308,177 | B1 | 10/2001 | Israni et al. |
| 6,415,295 | B1 | 7/2002 | Feinberg |
| 6,480,859 | B2 | 11/2002 | Mittal et al. |
| 6,507,840 | B1 | 1/2003 | Ioannidis et al. |
| 6,565,609 | B1 | 5/2003 | Sorge et al. |
| 6,606,744 | B1 | 8/2003 | Mikurak |
| 6,636,850 | B2 * | 10/2003 | Lepien .............................. 707/6 |
| 6,666,874 | B2 | 12/2003 | Heitzmann et al. |
| 6,701,345 | B1 | 3/2004 | Carley et al. |
| 6,816,880 | B1 | 11/2004 | Strandberg et al. |
| 6,988,075 | B1 | 1/2006 | Hacker |
| 2001/0051879 | A1 | 12/2001 | Johnson et al. |
| 2001/0051880 | A1 | 12/2001 | Schurenberg et al. |
| 2001/0051881 | A1 | 12/2001 | Filler |
| 2002/0007284 | A1 | 1/2002 | Schurenberg et al. |
| 2002/0073099 | A1* | 6/2002 | Gilbert et al. ............. 707/104.1 |
| 2003/0009446 | A1 | 1/2003 | Agarwal et al. |
| 2004/0019593 | A1* | 1/2004 | Borthwick et al. ................ 707/4 |
| 2004/0260694 | A1* | 12/2004 | Chaudhuri et al. ................ 707/5 |
| 2005/0108188 | A1* | 5/2005 | Santosuosso ...................... 707/1 |
| 2005/0210383 | A1* | 9/2005 | Cucerzan et al. ............. 715/533 |

FOREIGN PATENT DOCUMENTS

| | | |
|---|---|---|
| JP | 11203320 | 7/1999 |
| JP | 20022140364 | 5/2002 |
| WO | 98 13783 | 4/1998 |
| WO | WO9909729 A1 * | 2/1999 ............ H04M 1/274 |
| WO | 9944162 | 9/1999 |
| WO | 0000915 | 1/2000 |
| WO | 0065522 | 11/2000 |
| WO | 0102285 | 3/2001 |
| WO | 0122285 | 3/2001 |
| WO | WO 2004/049240 A1 | 6/2004 |

OTHER PUBLICATIONS

Cheng et al., "Adaptive Stream Filters for Entity-based Queries with Non-Value Tolerance Technical Report", Feb. 2005.*

"Processing real-time non-aggregate queries with time-constraints in CASE-DB", Ozsoyoglu et al, Data Engineering, 1992, Proceedings. Eighth International Conference on Tempe, AZ, USA, Feb. 2-3, 1992, Los Alamitos, CA, USA, IEEE Comput. Soc. US, Feb. 2, 1992, pp. 410-417.

Notification of Reasons for Refusal in JP Patent Application No. 2008-514799, dated Mar. 22, 2011.

Canadian Office Action of Application No. 2,609,916 dated Dec. 17, 2010.

Japanese OA in JP Patent Application No. 2008-514799 dated Aug. 3, 2010.

Aizawa, et al., "Techniques and Research Trends in Record Linkage Studies", vol. J88-D-I, No. 3, pp. 576-589 (partial English translation).

David Forslund and David Kilman, "The Virtual Patient Record: A Key to Distributed Healthcare and Telemedicine", Los Alamos National Laboratory, Feb. 29, 1996, printed from http://openemed.net/background/TeleMed/Papers/virtual.html on Jun. 1, 2007.

Kilman, "An international collaboratory based on virtual patient records", Aug. 1997, ACM Press, Communications of the ACM, vol. 40, issue 8, pp. 110-117.

Sheth, "Federated Database Systems for Managing Distributed, Heterogeneous, and Autonomous Databases", Sep. 1990, ACM Computing Survey, vol. 22, No. 3, p. 183-236.

Demers, "Epidemic algorithms for replicated database maintenance", Aug. 10, 1987, Proceedings of the sixth annual ACM Symposium on Principles of distributed computing, Vancouver, British Columbia, Canada, p. 1-12.

Daniel T. Heinze et al., "LifeCode: A Deployed Application for Automated Medical Coding", AI Magazine, Summer 2001, vol. 22, No. 2, ProQuest Computing, pp. 76-88.

Carleton Corporation, "The Four Challenges of Customer-Centric Data Warehousing", Internet Publication Online!, Nov. 1998 (Nov. 1991) XP002259648 16 pages.

M. Garcia, et al., "Immunization Registered DeDuplication and Record Matching," Internet Publication—Scientific Technologies Corporation Online! 1999, XP002259647, 12 pages.

Brelstaff, "Internet Patient Records: new techniques", Mar. 17, 2001, Journal Medicine Internet Res. Jan.-Mar. 2001; 3 (1): e8.

* cited by examiner

|   | Locator Field | Record Field | Distance Measure | Limit |
|---|---|---|---|---|
| 1 | First Name | First Name | FirstNameDistance | 5 |
| 2 | Last Name | Last Name | LastNameDistance | 5 |
| 3 | SSN | SSN | EditDistanceWithSwap | 4 |
| 4 | Gender | Gender | Exact | - |
| 5 | Marital Status | Marital Status | Exact | - |
| 6 | BirthYear | BirthYear | Exact | - |
| 7 | BirthMonth | BirthMonth | Exact | - |
| 8 | BirthDate | BirthDate | Exact | - |
| 9 | StreetName | StreetName | EditDistanceWithSwap | 4 |
| 10 | StreetNumber | StreetNumber | EditDistanceWithSwap | 2 |
| 11 | StreetDirection | StreetDirection | Exact | - |
| 12 | StreetSuffix | StreetSuffix | Exact | - |
| 13 | SecondaryUnitNum | SecondaryUnitNum | Exact | - |
| 14 | SecondaryUnit | SecondaryUnit | Exact | - |
| 15 | City | City | Exact | - |
| 16 | State | State | Exact | - |
| 17 | Zip | Zip | Exact | - |
| 18 | Home Phone | Home Phone | EditDistanceWithSwap | 3 |
| def |   |   | EditDistance | 2 |

FIG. 1

| | $c_j$ | 0 | 1 | 2 | 3 | 4 | 5 |
|---|---|---|---|---|---|---|---|
| $j$ | Field Name | | | | | | |
| 1 | First Name | 0.003 | 0.003 | 0.004 | 0.03 | 0.11 | 0.85 |
| 2 | Last Name | 0.003 | 0.003 | 0.004 | 0.01 | 0.07 | 0.91 |
| 3 | SSN | 0.001 | 0.002 | 0.003 | 0.004 | 0.99 | - |
| 4 | Gender | 0.5 | 0.5 | - | - | - | - |
| 5 | Marital Status | 0.25 | 0.75 | - | - | - | - |
| 6 | BirthYear | 0.02 | 0.98 | - | - | - | - |
| 7 | BirthMonth | 0.1 | 0.9 | - | - | - | - |
| 8 | BirthDate | 0.05 | 0.95 | - | - | - | - |
| 9 | StreetName | 0.001 | 0.002 | 0.003 | 0.004 | 0.99 | - |
| 10 | StreetNumber | 0.001 | 0.01 | 0.989 | - | - | - |
| 11 | StreetDirection | 0.3 | 0.7 | - | - | - | - |
| 12 | StreetSuffix | 0.1 | 0.9 | - | - | - | - |
| 13 | SecondaryUnitNum | 0.1 | 0.9 | - | - | - | - |
| 14 | SecondaryUnit | 0.45 | 0.55 | - | - | - | - |
| 15 | City | 0.42 | 0.58 | - | - | - | - |
| 16 | State | 0.5 | 0.5 | - | - | - | - |
| 17 | Zip | 0.01 | 0.99 | - | - | - | - |
| 18 | Home Phone | 0.003 | 0.003 | 0.004 | 0.99 | - | - |
| def | | 0.2 | 0.3 | 0.5 | - | - | - |

FIG. 2

| $c_j$ j | | 0 | 1 | 2 | 3 | 4 | 5 |
|---|---|---|---|---|---|---|---|
| | FieldName | | | | | | |
| 1 | First Name | 0.6 | 0.2 | 0.1 | 0.06 | 0.03 | 0.01 |
| 2 | Last Name | 0.6 | 0.2 | 0.1 | 0.06 | 0.03 | 0.01 |
| 3 | SSN | 0.7 | 0.15 | 0.09 | 0.05 | 0.01 | - |
| 4 | Gender | 0.9 | 0.1 | - | - | - | - |
| 5 | Marital Status | 0.9 | 0.1 | - | - | - | - |
| 6 | BirthYear | 0.9 | 0.1 | - | - | - | - |
| 7 | BirthMonth | 0.9 | 0.1 | - | - | - | - |
| 8 | BirthDate | 0.9 | 0.1 | - | - | - | - |
| 9 | StreetName | 0.7 | 0.15 | 0.09 | 0.05 | 0.01 | - |
| 10 | StreetNumber | 0.9 | 0.9 | 0.01 | - | - | - |
| 11 | StreetDirection | 0.55 | 0.45 | - | - | - | - |
| 12 | StreetSuffix | 0.55 | 0.45 | - | - | - | - |
| 13 | SecondaryUnitNum | 0.9 | 0.1 | - | - | - | - |
| 14 | SecondaryUnit | 0.55 | 0.45 | - | - | - | - |
| 15 | City | 0.9 | 0.1 | - | - | - | - |
| 16 | State | 0.9 | 0.1 | - | - | - | - |
| 17 | Zip | 0.9 | 0.1 | - | - | - | - |
| 18 | Home Phone | 0.7 | 0.15 | 0.09 | 0.06 | - | - |
| def | | 0.5 | 0.3 | 0.2 | - | - | - |

FIG. 3

| PersObjId | FN | LN | AddressLine1 | Ph # | Curr. Name? | Curr. Addr.? | Curr. Ph.? |
|---|---|---|---|---|---|---|---|
| 3 | John | Smith | 456 Peachtree Ave. | 222-333-4444 | False | False | False |
| 3 | John | Smith | 456 Peachtree Ave. | 123-456-7890 | False | False | True |
| 3 | John | Smith | 123 Main St. | 222-333-4444 | False | True | False |
| 3 | John | Smith | 123 Main St. | 123-456-7890 | False | True | True |
| 3 | Jack | Smythe | 456 Peachtree Ave. | 222-333-4444 | True | False | False |
| 3 | Jack | Smythe | 456 Peachtree Ave. | 123-456-7890 | True | False | True |
| 3 | Jack | Smythe | 123 Main St. | 222-333-4444 | True | True | False |
| 3 | Jack | Smythe | 123 Main St. | 123-456-7890 | True | True | True |

FIG. 4

| PersObjId | FN | LN |
|---|---|---|
| 3 | John | Smith |
| 3 | Jack | Smythe |

FIG. 5

| PersObjId | FN | LN | AddressLine1 | Ph # | Score |
|---|---|---|---|---|---|
| 3 | John | Smith | 123 Main St. | 123-456-7890 | 90 |
| 3 | Jack | Smythe | 123 Main St. | 123-456-7890 | 85 |

FIG. 6

SYSTEM AND METHOD FOR DATA SENSITIVE FILTERING OF PATIENT DEMOGRAPHIC RECORD QUERIES

CROSS REFERENCE TO RELATED UNITED STATES APPLICATION

This application claims priority from "Data Sensitive Filtering in Search for Patient Demographic Records", U.S. Provisional Application No. 60/686,065 of Phan, et al., filed May 31, 2005, the contents of which are incorporated herein by reference.

TECHNICAL FIELD

This invention is directed to the searching and filtering of medical record database queries.

DISCUSSION OF THE RELATED ART

An important functionality of a hospital information system is the ability to perform an error-tolerant search for a patient's record based on some input criteria. For example, hospital staff members frequently need to identify a patient based on as little as last name, first name and/or date of birth.

Two requirements of such a search are: (1) the search should be error tolerant because the search criteria may have errors, as compared with stored values in the hospital database; and (2) the search should terminate within a specified time, e.g. 1-2 seconds. These two requirements are competitive in a sense that more error tolerance requires longer response time. Suppose for example that a scoring algorithm can compare 10,000 records against search criteria each second and that the time allotted for scoring is 1 second. Then, in order to keep the response time within the specified limit, the system can retrieve at most 10,000 records of high potential from a demographic database containing possibly millions of records.

Normally, one can retrieve an appropriate pool of records for more detailed scoring by setting a filter that is a predefined condition that must be satisfied by a database record. Basically, one assumes that at least certain parts of the search criteria are correct and based on that information retrieve records from the database. In the example of search by last name and first name, a filter could be set by assuming that the first 4 characters of the first name and/or first 5 characters of the last name in the search criteria are correct. Therefore, the retrieved pool consists only of records that have the first 4 characters in the first name field and/or 5 characters in the last name field as the search criteria. Notice that the two logical connectors, AND and OR, have different effects on the number of records retrieved and on error tolerance. The AND connection assumes that both 4 characters of the first name and 5 characters of the last name are correct, but the number of records to be retrieved will be much fewer than using the OR connection, which however is more error tolerant because it assumes only either 4 characters of the first name or 5 characters of the last name are correct.

A disadvantage of this method is that by fixing filter positions in advance the size of the pool will vary greatly depending on the frequency of the search values. For example, the filter would retrieve too many records for search criteria "James Smith" while retrieving too few for search criteria "Zbigniew Brzezinski". In the former case, the time needed to complete the search could exceed the specified response time. In the latter case, the intended "true" record may fail to be included to the pool (therefore the search will fail) if a typographic error occurs in the first few characters of "Zbig" or "Brzez".

SUMMARY OF THE INVENTION

Exemplary embodiments of the invention as described herein generally include methods and systems for data-sensitive filtering to retrieve high potential records from demographic database for comparison with an input criteria in searching for a patient's demographic record. The filter allows maximum error tolerance while keeping the response time within specified limit. A data sensitive filter according to an embodiment of the invention uses a filtering condition that is dependent on the frequency of the search values. These frequencies can be pre-computed and re-calculated periodically (e.g. monthly, yearly) as the database is updated. For example, in case of searching for "James Smith", the filter should know that there are too many "James Smith" entries in the database and that it should use a stricter filtering condition or ask for additional information. In case of "Zbigniew Brzezinski" the filter should know that it is a rare name and relax the filter condition for example by assuming that only 2 first characters in the first name are correct (instead of 4) and that only the first 3 characters in the last name are correct (instead of 5). This kind of filter is maximizes error tolerance while guaranteeing a response time to be within limits.

According to an aspect of the invention, there is provided a method for data sensitive filtering in patient database searches, including providing a search criteria comprising one or more search locator fields, determining a retrieval formula from said search criteria that maximizes error tolerance in said search criteria while satisfying a predefined response time requirement, retrieving said candidate records from said database, wherein if no retrieval formula can be found to satisfies said response time requirements, requesting additional search criteria, scoring each said candidate record by comparing a search criteria locator field with a corresponding retrieved record field, determining whether said score of said candidate record exceeds a predefined threshold, and if said candidate score does exceed said threshold, adding said candidate record to a list of records to be returned in response to said search criteria.

According to a further aspect of the invention, the search criteria includes a first name and a last name, the method further comprising compiling a list of names equivalent to said first name in said search criteria.

According to a further aspect of the invention, comparing a search criteria locator field with a corresponding candidate record field comprises performing a field by field comparison of said locator field and said candidate record field pair to fill in components of a comparison result vector $c_j$ for a field pair j using a field comparison method predefined for each field pair for up to a predefined number of characters in said pair of fields, scoring said comparison result $c_j$ based on one or more probabilities using a formula $$\text{score}(c_j) = \log(P_{1j}(c_j)) - \log(P_{0j}(c_j)) = \log\left(\frac{P_{1j}(c_j)}{P_{0j}(c_j)}\right),$$

wherein $P_{0j}(c_j)$ and $P_{1j}(c_j)$ are probabilities that are functions of the number of matching characters in said pair of fields, and summing score($c_j$) over all fields j where the both the locator field and the corresponding field in said candidate record are not blank to calculate a first score.

According to a further aspect of the invention, if both a first name and a last name are specified in the search criteria, swapping said first and last names in the search criteria, repeating said steps of performing a field by field comparison of the swapped locator field with the candidate record field, scoring said comparison result $c_j$, and summing said score over all fields j to calculate a second score, and selecting a maximum of said first score and said second score minus a swap penalty.

According to a further aspect of the invention, the method comprises transforming said score to a 0 to 100 scale according to a formula $$transformedScore=(score-minScore)/(maxScore-minScore)\%100$$

wherein maxScore=$\Sigma_j$ maxScore$_j$, minScore=$\Sigma_j$ minScore$_j$, wherein the locator field that is used to generate the $j^{th}$ component of the comparison vector is not blank in the search criteria, and wherein maxScore$_j$=max(score($c_j$)) and minScore$_j$=mi(score($c_j$)) over all possible values of $c_j$.

According to a further aspect of the invention, the field comparison method for a field is one of an exact distance match, a Hamming distance, and edit distance, and edit distance with swap, a first name distance, and a last name distance.

According to a further aspect of the invention, the method comprises, for each candidate record in said list of records to be returned, retrieving a most recent complete record from said database for said search locator field, for each field that has a non-empty value in said candidate record, replacing the field value in the retrieved complete record with the corresponding value in the candidate record, and adding the altered complete record to said database.

According to another aspect of the invention there is provided a method for data sensitive filtering in patient database searches, including providing a search criteria for retrieving one or more records from a database comprising one or more search locator fields, determining a maximum number of candidate records to be retrieved from said database, and a maximum response time for retrieving said records, determining a number of candidate records to be retrieved based on a number of characters in said search criteria being correct, determining a retrieval formula from said search criteria that maximizes error tolerance in said search criteria while satisfying said response time requirements, and retrieving said candidate records from said database, wherein if no retrieval formula can be found to satisfies said response time requirements, requesting additional search criteria.

According to a further aspect of the invention, if a number of candidate record retrievable using said retrieval formula falls below a minimum number of candidate records, reducing said number of characters in said search criteria assumed to be correct.

According to a further aspect of the invention, the maximum number of candidate records to be retrieved is determined from a frequency table of database values that represent probabilities of search criteria fields being included in said database, and wherein strings having probability values higher than a predefined threshold are stored in memory.

According to a further aspect of the invention, the threshold is based on the database size, required response time, and a speed of comparison between said search criteria and said candidate records.

According to a further aspect of the invention, the probabilities include probabilities of search criteria sub-fields being included in said database.

According to a further aspect of the invention, the method comprises comparing said search criteria with a first candidate record and storing a result of said comparison and said first candidate record in a table, searching for each subsequent candidate record by searching said table, wherein if said subsequent candidate record is not found in said table, comparing said subsequent candidate record with said search criteria and storing said comparison result and said subsequent candidate record in said table.

According to a further aspect of the invention, the retrieval formula comprises a logical formula formed from said one or more search locator fields.

According to a further aspect of the invention, if said search criteria includes only one search field, basing said retrieval formula on a sub-string of said search field, and searching a dictionary of high frequency strings, and performing a database query if said search sub-string is not found in said dictionary.

According to a further aspect of the invention, if said search criteria includes more than two search fields, forming said logical formula from a disjunction of conjunction of pairs of search criteria.

According to a further aspect of the invention, if said search criteria includes two search fields, forming said logical formula from logical combinations of comparisons of the entire search fields and comparisons of partial search fields.

According to another aspect of the invention, there is provided a program storage device readable by a computer, tangibly embodying a program of instructions executable by the computer to perform the method steps for data sensitive filtering in patient database searches.

BRIEF DESCRIPTION OF THE DRAWINGS

FIG. 1 is a table of field comparison methods, according to an embodiment of the invention.

FIG. 2 is a table of exemplary values of the probabilities $P_{0j}(c_j)$, according to an embodiment of the invention.

FIG. 3 is a table of exemplary values of the probabilities $P_{1j}(c_j)$, according to an embodiment of the invention.

FIG. 4 is a table illustrating database rows with a person's name, address and phone fields joined, according to an embodiment of the invention.

FIG. 5 is a table depicting exemplary candidates for John Smythe, according to an embodiment of the invention.

FIG. 6 is a table illustrating exemplary query results reported for John Smythe, according to an embodiment of the invention.

DETAILED DESCRIPTION OF THE PREFERRED EMBODIMENTS

Figure 7:
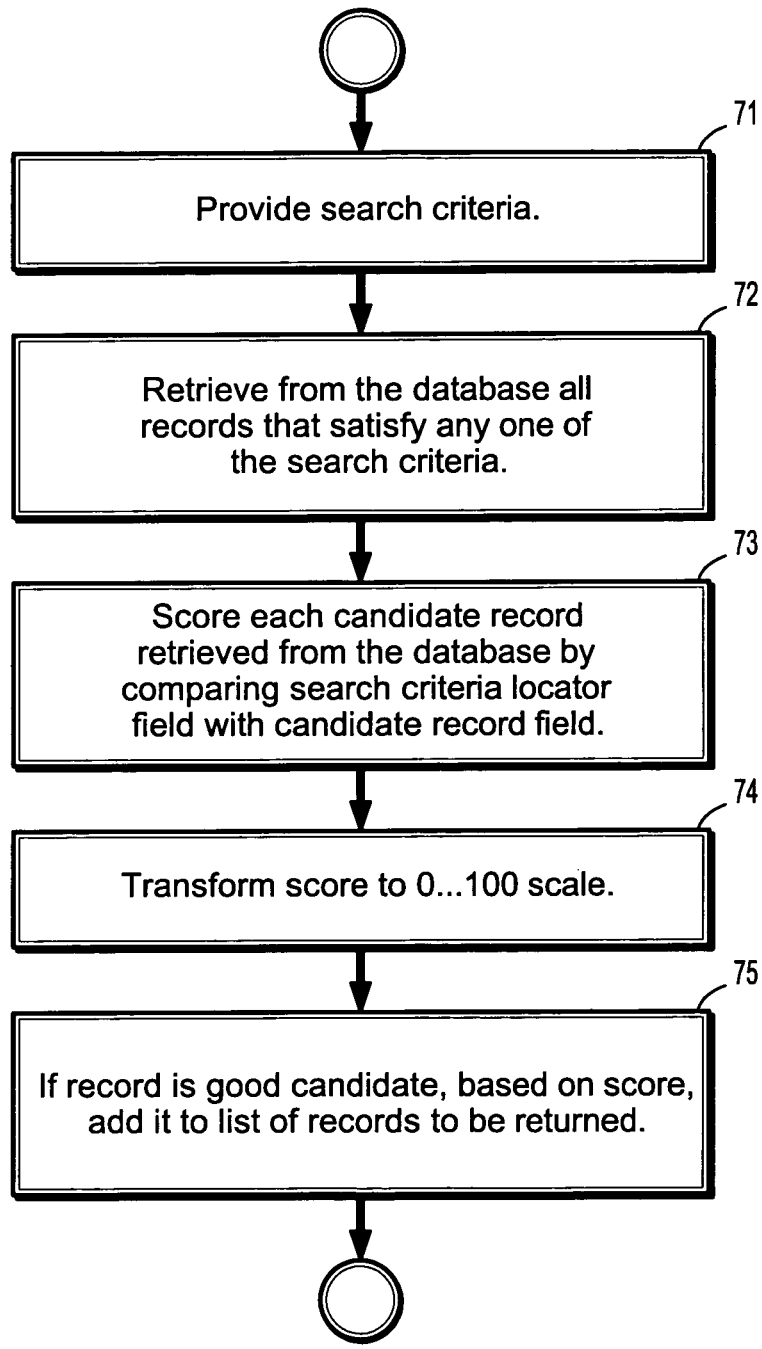
FIG. 7 is a flow chart of data sensitive retrieval filtering process according to an embodiment of the invention.

Exemplary embodiments of the invention as described herein generally include systems and methods for data sensitive filtering of searches for patient demographic records. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Some medical databases store the history of all fields, so that a record retrieval should search the historical records as well. According to an embodiment of the invention, the demographic record of a person with historical information can be treated as being several records: for example, if there are 3 names, 2 addresses but only 1 value for every other demographic field for a person, then there will be 6 demographic records this person. It can be assumed that there will be a means of retrieving the most recent information for a given person, which shall be used to return a list of top candidates.

In addition, some databases support having multiple values for certain fields, such as name (legal, alias, pseudo) and address (residence, mailing, billing). The data structures representing demographic information should distinguish between the different fields. For convenience of retrieval and scoring, an algorithm according to an embodiment of the invention treats all these variants in a symmetric manner. Variants of a field are treated in exactly the same way as the historical values of that field.

In addition, values derived from the demographic records can be used to retrieve records for scoring. These demographic records are referred to as record linkage (RL) keys. For example, one can form a new string by concatenating the first 4 characters of a Last Name with last 4 characters of a Given Name and storing that in a database so that later one can use it to find a data row without calculating. According to an embodiment of the invention, the values of the RL keys will be pre-computed for the "most recent" values of the respective fields. This pre-computation can be extended to computing and storing historical values.

According to an embodiment of the invention, a exemplary medical database D has n records, with each record having m fields $F_1, F_2, \ldots, F_m$. An exemplary retrieval request from this database involves retrieving records based on one or more strings $s_1, \ldots, s_I$ that represent possibly noisy values of the fields $F_1, \ldots, F_I$ of a record.

An answer to this request includes 2 parts:

(1) In a first part, a logical formula $\Phi$ is formed on the basis of the requested fields and input values. This formula is placed as an SQL query to retrieve data from database D. This results in a set of k records.

(2) In a second part, the k retrieved records are scored.

The cost of the solution is measured by the time needed to complete the request and by the desired accuracy. There is also a requirement that the total request processing time be less that some upper limit T:

Total time=retrieval time+scoring time,

Scoring time=$k \% a$, where k is the number of records retrieved and a is the time needed for each scoring. Retrieval time is also sensitive to the number of records, although the dependence may not be linear. From the performance requirement one can roughly calculate the maximal number k that should be retrieved. There are several possible retrieval formulae.

One formula involves logical disjunction of simple logical formulae:

$\Phi = (F_1 = s_1) \vee (F_2 = s_2) \ldots \vee (F_I = s_I)$.

This formulation ensures that when at least one string is a correct value, then the intended record will be retrieved and scored.

Let $X_i$ be the number of errors in string $s_i$. For a simple logical formula $\phi$, let $S(\phi)$ be the number of records that satisfy $\phi$. Then, the probability that $\Phi$ fails to retrieve the intended record is $$F(\Phi) = \prod_{i=1}^{I} P(X_i \geq 1),$$

and the number of records retrieved using $\Phi = \phi_1 \vee \phi_2 \ldots \vee \phi_I$ is $$S(\Phi) = \sum_{i=1}^{I} S(\phi_i) - \sum_{i,j} S(\phi_i \& \phi_j) + \sum_{i,j,k} S(\phi_i \& \phi_j \& \phi_k) - \ldots$$

For example, if I=3, $\Phi = \phi_1 \vee \phi_2 \vee \phi_3$, and $$S(\Phi) = \sum_{i=1}^{3} S(\phi_i) - S(\phi_1 \& \phi_2) - S(\phi_2 \& \phi_3) - S(\phi_3 \& \phi_1) + S(\phi_1 \& \phi_2 \& \phi_3).$$

Another formulation involves logical conjunction:

$\Psi = (F_1 = s_1) \& (F_2 = s_2) \ldots \& (F_I = s_I)$.

In this case, the probability that the intended record will not be retrieved is $$F(\Psi) = 1 - \prod_{i=1}^{I} P(X_i = 0),$$

and the number of records retrieved is $S(\Psi) = S(\phi_1 \& \phi_2 \ldots \& \phi_I)$.

As an example of the use of these formulae, consider a database with $n=10^6$ records, and probabilities $P(\phi_1)=0.04$, $P(\phi_2)=0.03$, and $P(\phi_3)=0.02$. This implies that $S(\phi_1)=4\%10^4$, $S(\phi_2)=3\%10^4$, and $S(\phi_3)=2\%10^4$. Suppose that strings $s_1, s_2, s_3$ having lengths 2, 6, and 4, respectively, are entered with an error rate of 0.05. Then, the probabilities that no error occurs in $s_1, s_2, s_3$ are, respectively, 0.5404, 0.7351, and 0.8145.

Using $\Phi$ as a retrieval formula, one has $S(\Phi)=8.7 \times 10^4$ and $F(\Phi)=0.0226$.

Using $\Psi$ as a retrieval formula, one has $S(\Psi)=24$, and $F(\Psi)=0.6765$.

This example illustrates that retrieval formulae using only OR-logic as well as using only AND-logic might not yield satisfactory results for opposite reasons. OR-logic leads to too many records that need to be retrieved and scored, while AND-logic leads to too high of a probability of failure to capture the intended record.

One strategy to improve upon this scenario is to use a formula that is a disjunction of conjunctions of a smaller number of terms. For example, in the I=3 case, one would have:

$$\Gamma = (\phi_1 \& \phi_2) v (\phi_2 \& \phi_3) v (\phi_3 \& \phi_1).$$

This yields for the above example:

$$S(\Gamma) = 2.6\% 10^4,$$

and $$F(\Gamma) = 0.2110.$$

The formulation of using disjunction of conjunction does not apply for the case of I=2. The previous retrieval formulae were based on comparison of an entire string against the field values. Another formulation is based on comparison of a part of a field value. Let $s(i)$ represent the $i^{th}$ character of a string and $s(i,j)$ represent the substring of s that starts at i and ends at j.

Consider a retrieval formula of the form:

$$\Delta = ((F_1 = s_1) \& (F_2(i,j) = s_2(i,j))) v ((F_1(i,j) = s_1(i,j)) \& (F_2 = s_2)).$$

For example, if i=j=1, $\Delta$ retrieves all records with first field equal to $s_1$ and first character of second field equal to the first character of $s_2$, or with the second field equal to $s_2$ and the first character of the first field equal to the first character of $s_1$.

If it is assumed that the probability of the first character of field $F_i$ is x, then $P(F_i(1) = x) = 0.1$. This is a conservative estimate since there are 26 letters in the alphabet.

This partial comparisons formulation ca be applied to calculate $S(\Delta)$ and $F(\Delta)$ for the numerical example above:

$$S(\Delta) = 0.58 \times 10^4 = (0.04 \times 0.1 + 0.03 \times 0.1 - 0.04 \times 0.03) \times 10^6,$$

$$F(\Delta) = 0.1855 = 1 - (0.5404 \times 0.95 + 0.7351 \times 0.95 - 0.5404 \times 0.7351).$$

In contrast, for $\Phi = (F_1 = s_1) v (F_2 = s_2)$:

$$S(\Phi) = 6.88 \times 10^4 = (0.04 + 0.03 - 0.04 \times 0.03) \times 10^6,$$

$$F(\Phi) = 0.1218 = (1 - 0.5404) \times (1 - 0.7351),$$

and for $\Psi = (F_1 = s_1) v (F_2 = s_2)$:

$$S(\Psi) = 0.12 \times 10^4 = (0.04 \times 0.03) \times 10^6,$$

$$F(\Psi) = 0.6028.$$

The $\Delta$ formulation ca be extended to a form that handles 4 parameters i,j,h,k as follows:

$$\Delta(i,j,h,k) = ((F_1(i,j) = s_1(i,j)) \& (F_2(h,k) = s_2(h,k))).$$

This formula takes $q = (j-i) + (k-h)$ characters (j-i) of string $s_1$ and (k-h) of $s_2$ to compare with the corresponding values of the fields. Using two groups of characters for different strings (fields) in general is more efficient than taking the same number of characters from one'string. The reason is that while it is reasonable to assume that two groups of characters in two strings are independent, it is not reasonable to make the assumption for groups of characters in the same string. For example, "Smith" is a common last name (the probability P(LastName="Smith")=0.03), but the conditional probability P(LastName(4,5)="th" |LastName(1,3)="Smi") is high (0.3).

Note that identification of a character to compare is not necessarily restricted to the natural position within a string. It can be from left or from the right, and may count only consonants or only vowels, or any subset of the alphabet. In addition, the selections of characters should ensure that the assumption of independence is reasonable.

The case of only one input string $s_1$ presents different challenges. If $S(F_1 = s_1)$ is too large, it makes sense to detect this condition before spending time on searching. Suppose the maximum number of records that can be scored within the time limit is $k_m$. A list of field values whose frequency is greater than $k_m$ can be stored, and a given string $s_1$ can be checked against that list before launching a SQL retrieval. The number of such values is less than $n/k_m$. The probability that a search on the whole string fails to retrieve the intended record is $$1 - (1-r)^l,$$

where r is the error rate and l is the length of the input string. Most of the time, the issue is not that $S(F_1 = s_1)$ is too large, but rather that the probability of failure is too high. For example, if s is an entered last name of length 15 and the error rate is 0.05, then F(LastName=s)=0.5367. If such a failure level is not acceptable, then search conditions should be relaxed. For example, the search condition $F_1(i,j) = s(i,j)$ can be used. If j-i=5 then the probability that the intended record fails to be retrieved is reduced to 0.2262.

Thus, when a search condition is one string, a partial search on the search is a better approach. For example, rather than searching for the whole string, it is better to use the first 5 or 6 characters as the database search criteria. In order to avoid retrieving too many records, a dictionary of high-frequency strings should be built, possibly before the first run. A user's search is then filtered through the dictionary before getting to the SQL query. If the user's search string is found in the dictionary, no SQL query will be issued and the user will be asked for more information. Note that for retrieval formulae using partial comparisons, the partial strings should be precomputed.

When a user provided 2 strings, retrieval formulae $\Delta(i,j,h,k)$ provide a better balance between the number of records to retrieve and score and the error tolerance. When a use provides more than two strings, the disjunction of conjunction formulae are good search candidates.

According to an embodiment of the invention, as a preliminary step, frequency information of database values should be collected. A set of character positions can be predefined within a string for each field on which patient searched are applied. For fields on which a patient search is applied, all records will be scanned and the frequency of all values will be counted. For example, suppose a patient search could be based on combinations of fields: for example, Last name, First name, Date of birth, Home address, medical record number (MRN) and Social Security number (SSN). The sets of positions can be arbitrary, but for sake of simplicity, one can assume that the positions selected are consecutive and count from the left (beginning) or right (end) of a string. Given a set of positions, the frequency of each distinct value is counted. A scan through a database counts frequencies of the following non-limiting, exemplary string values that are formed by first i characters of Last name, First name, Date of birth, Home address and last i characters of MRN, SSN. Value i can be 3, 4 and 5. For example, for i=4 and First name field, the frequency for string "adle" counts given names "Adler", "Adley", "Adleen" etc.

The string frequencies then are converted into probabilities (proportions) by dividing the counts by the size of database. The probabilities are more stable over a period of time than the number of counts as the database itself gets updated.

These two steps are repeated periodically or whenever the database undergoes a significant update merger to reflect its current state.

Those strings that have probabilities higher than a predefined threshold are stored in memory. The threshold is determined based on the database size and required response time and comparison speed. For example, if it is desired to keep only strings that have a frequency count higher than 100 for database of size 1 million records, the threshold is set at $10^2/10^6=10^{-4}$. That is, only strings that have frequency higher than 100 are kept. Any string not found in the table can be assumed to have a very low frequency. The heavy skewness of distribution of realistic names means the number of strings satisfying this condition is often less than a few hundred. On the other hand, if one finds that the distribution of, e.g. the last 4 digits of the social security number (SSN) is practically uniform, (i.e. the probability of any string of 4 digits is the same), then one stores only that probability value.

A flow chart of data sensitive retrieval filtering process according to an embodiment of the invention is depicted in FIG. 7. Assuming that frequency information of database values has been tabulated, a search criteria is provided at step 71. The search criteria can comprise one or more strings of field values to be matched with appropriate records in a medical demographic database. Given this search criteria, the database search engine looks into frequency table to determine how many records the pool will have for each filtering formula if one assumes i characters of search criteria are correct and what logical connections are used. Once the search criteria have been accepted, the search criteria are normalized to break out the phone number, address, SSN, etc.

A table of exemplary field comparisons according to an embodiment of the invention is depicted in FIG. 1. This table shows 18 possible search criteria, one for each numbered row in the table. It should be noted that this selection of search criteria is exemplary and non-limiting, and more or fewer search criteria can be used according to an embodiment of the invention. The column labeled "Locator field" corresponds to locators provided with the search criteria, while the column labeled "Record Field" corresponds to records in the database. The column labeled "Distance Measure" indicates the field comparison method used to compare the locator and record of that row, and the last column, labeled "Limit", indicates the number of characters used in the comparison. The last row in the table indicates that a default comparison uses the EditDistance comparator with 2 characters.

From the search field configuration information, a list of names equivalent to the first name specified in the search criteria are retrieved, i.e., the list of all the names that belong to at least one of the groups that the specified first name belongs to. A person's first name may have different variations. For example, Robert-Bob-Bobby, or Theodore-Ted-Ed. Such name variations are considered equivalent. When a user wants to find Bob White, one should consider Robert White and Bobby White as worthwhile candidates. This list is referred to as sc.equivalentFirstNameList.

In addition, in an embodiment of the invention, a phonetic encoding of the last name can be computed, for those databases that support searches based on those encodings.

Referring again to FIG. 7, at step 72, all demographic records where any one of the conditions listed below is true are retrieved from the database (here rec. refers to a record in the database, and sc. refers to the search criteria). As only the fields that are specified in the search criteria are used in scoring, only those fields that have been specified in the search criteria are retrieved for the candidates in order to prevent inefficiencies due to expensive joins in the retrieval process.

As an example, suppose the search criteria are "John Deer". Suppose the probability of string "john" is 0.01 and probability of string "Dee" is 0.015 in a database of 1 million records. The following situations are possible:
  a) If one assumes that first 4 characters in first name are correct, then the pool will have 1,000,000%0.01=10,000 records.
  b) If one assumes that the first 3 characters of last name are correct, then the pool will have 15,000 records.
  c) If one assumes that first 4 characters of first name are correct AND the first 3 characters of last name are correct, then the pool size is 1,000,000%0.01%0.015=150.
  d) If one assumes that first 4 characters of first name are correct OR the first 3 characters of last name are correct, then the pool size is estimated to be about 1,000,000% (0.01+0.015−0.01%0.015)=24,850λ25,000.

Suppose in order to meet a response time requirement, the pool of records retrieved should not exceed 10,000. Then it is desired to find-a filtering condition (logical formula) that allows maximum error tolerance while keeping the pool size within limits. For example, option (a) above is the best because it offers most error tolerance while satisfying time response requirement. Options (b) and (d) would be excluded because the pool would be too large. Option (c) is less preferable than (a) because for example if an error occurs in $3^{rd}$ character (the correct name is John Dear) then (c) would fail to retrieve the record while (a) still does.

In some cases it can happen that none of available options deliver a pool of less than 10,000. For the example of the search for "James Smith", if the probability of "jame" is 0.12 and the probability of "smi" is 0.1, even option (c) using the AND connection would have 1,000,000%0.12%0.1=12,000. This means that the search could not be completed within specified time. Unless the user accepts longer response time, the system should ask for more information, for example Home address, and uses that information to restrict further the pool. For example, if the home address is "123 Main St", then one does not retrieve records from database by "Jame"+"Smi" but by "Jame"+"Smi"+"Main". The best filter would be one that retrieves records by the first 4 characters of the home address, which results in 1,000,000%0.009=9,000 records.

In case of rare names like "Zbigniew Brzezinski", with the probability of "zbig"=0.00001 and the probability of "brz"=0.0001, even the option assuming 4 characters of first name OR 3 characters of last name will result in only about 1,000,000%(0.0001+0.0001)=110 records. In this case, one can relax the assumption by assuming only 3 characters of first name or 3 characters of last names are correct. That tolerates the error in the $4^{th}$ character of first name.

An exemplary, non-limiting list of conditions according to an embodiment of the invention is as follows. An "(RL key)" following a condition indicates that the condition is a precalculated record linkage.
  a. Names:
    i. Sc.lastname=rec.lastname
    ii. Sc.firstname=rec.firstname
    iii. Sc.lastnamephonetic=rec.lastnamephonetic (RL key)
    iv. Sc.lastname has length>=4 AND rec.lastname starts with sc.lastname
    v. (includeNickNameInQuery=true) AND Rec.firstname is present in sc.equivalentFirstNameList vi. Rec.firstname=sc.lastname AND rec.lastname=sc.firstname
vii. Sc.lastNameFirst4Chars=rec.lastNameFirst4Chars (RL key)
b. Address
   i. Sc.addressLine1=rec.addressLine1
   ii. Sc.houseNo=rec.houseNo (RL key)
   iii. Sc.streetName=rec.streetName (RL key)
c. Phone Number
   i. sc.phoneNo=rec.phoneNo (7 digits after area code, RL key)
d. Date of birth
   i. Sc.birthMonth=rec.birthMonth AND sc.birthDate=rec.birthDate AND sc.birthYear=rec.birthYear
e. Person Identifiers
   i. Sc.SSN=rec.SSN
   ii. Sc.SSNLast4Chars=rec.SSNLast4Chars (RL Key)
   iii. Sc.personNumber=rec.personNumber
   iv. Sc.medicalRecordNumber=rec.medicalRecordNumber At step 73, each candidate record retrieved from the database is scored as follows. The given locator is compared with the candidate to generate a comparison vector having a component for search criteria field. A field vs. field comparison is performed to fill in the components of the comparison vector. According to an embodiment of the invention, the field comparison methods listed in FIG. 1 are used. The field comparison methods in this list are exemplary and non-limiting, and other field comparison methods can be used in other embodiment of the invention. For each specified search criterion that is not explicitly listed in the comparison configuration, a default comparison method is used to compare that field with the same field in the record retrieved from the database.

Fields are compared by computing the specified string distance between them, with the added constraint that the distance saturates at a given (field dependent) upper limit. Any distances larger than this upper limit are set to the limit e.g., first names are compared using edit distance (5) (described below) means that the result of comparison of the first names in two records is the edit distance between them if this distance is less than 5, else it is set to 5.

A list of exemplary, non-limiting string distance functions for field comparisons (all string metrics are case insensitive) is as follows.

a. Exact Match Distance: 0 when strings match exactly, else it is 1.
b. Hamming Distance: counts the number of places in which two strings of the same length differ (e.g. distance between 1000 and 1010 is 1, and that between 1000 and 0100 is 2). If the lengths of the two strings are different, then the distance should be the sum of the difference in lengths and the Hamming distance between the shorter string, and the prefix of the longer string of length equal to that of the shorter string.
c. Edit Distance: counts the smallest number of basic (single character) edit operations (insertion, deletion, replacement) required to transform one string into the other (e.g., distance between John and Jon is 1, John and Jonh is 2, John and Jo is 2).
d. Edit Distance With Swap: includes swapping adjacent characters as an extra operation in the above definition. (Note that the implementation being used is wrong as per this definition, but is good enough for our application as it may be correct under the assumption that any character position is involved in at most one swapping operation).
e. First Name Distance: If the two strings are equal, the distance is 0, if one is a prefix of the other, or there is a group of commonly used names that includes both strings, then the distance is 1, else it is the edit distance with swap between the two.
f. Last Name Distance: If the two strings are equal, the distance is 0, else if one is a prefix of the other, then the distance is 1, if the edit distance is greater than 2 and the two strings have the same phonetic encoding, then the last name distance is 2, else it is the edit distance with swap between the two.

Next, the comparison vector is scored using the probability information specified in the configuration file to obtain a score. An exemplary, non-limiting formula used for scoring a comparison result $c_j$ for a field j is:

$$\text{score}(c_j) = \log(P_{1j}(c_j)) - \log(P_{0j}(c_j)) = \log\left(\frac{P_{1j}(c_j)}{P_{0j}(c_j)}\right),$$

and bScore is defined as the sum of score($c_j$) over all j where the both the locator field and the corresponding field in the demographic record are not blank. The probability parameters $P_{ij}(c_j)$ in the formula reflect string frequencies and data quality, and the range of values taken by $c_j$ also depends on the comparison methods used.

Exemplary values for first probabilities $P_{0j}(c_j)$ and second probabilities $P_{1j}(c_j)$ are displayed in the tables of FIGS. 2 and 3. The format of each of these tables is the same. Referring to FIG. 2, the index j refers to the row number (i.e. search criteria locator field), and up to 5 columns of numbers are displayed to the left of the corresponding field name. The 5 columns correspond to the fact that according to an embodiment of the invention the maximum number of characters used for a field retrieval is 5 characters, as seen in the "Limits" column of the table of FIG. 1. For a given row, proceeding from left to right, the probability values monotonically increase, reflecting a higher probability of a match between the locator field and the record field as there are characters in common. Thus, referring to the "First Name" field, if only the first characters of the locator field and the record field match, the probability value is low: 0.003, while if the first 5 characters match, the probability value is higher: 0.85.

If both first and last names are specified in the search criteria, the first and last names are also swapped in the search criteria and the new search criteria is scored against the record by repeating steps of comparing the locator with the candidate and scoring the comparison vector to obtain cScore. The score of the candidate is set to max(bScore, cScore-swapPenalty). The SwapPenalty is initially set to log(10). Note that all comparison results from the bScore computation that do not involve names can be reused, and do not have to be recomputed.

Referring back to FIG. 7, the score is now transformed to a 0-100 scale at step 74. This is done based on the fields specified in the search criteria. The transformed score is defined as transformedscore=(score−minScore)/(maxScore−minScore)%100 where score is that obtained in the previous step, and max-Score and minScore are the maximum and minimum possible achievable scores for the specified search criteria and are defined below. A maximum score is defined by maxScore$_j$=max(score($c_j$))

over all possible values of $c_j$. For a given set of search criteria, maxScore is defined as the sum of maxScore$_j$ over all j where the locator field that is used to generate the $j^{th}$ component of the comparison vector is not blank in the search criteria. Similarly, minScore$_j$ and minScore are defined for a set of search criteria. Note that for each j, maxScore$_j$ and minScore$_j$ can be computed at startup time, and that maxScore and minScore need to be computed once for each search based on which criteria are specified.

If, at step 75, the record represents a "good" candidate, it is added to a list of records to return. According to an embodiment of the invention, a candidate is considered good if the transformed match score exceeds a configured threshold which is initially set to 65. For each candidate record in the list of records to return, the complete "most recent" record for that person identifier is retrieved. For each field that has a non-empty value in the candidate record, the value in the now retrieved complete record is replaced with that in the candidate record.

An exemplary table depicting database rows with a person's name, address, and phone number fields joined, is shown in FIG. 4. Referring now to the figure, the table has 8 rows of data for a search query for John Smythe. The first column, labeled "PersObjId", depicts a identification number for the subject being sought by the query. The second column, "FN", list a first name, the third column, "LN", lists a last name, the fourth column, "AddressLine1", lists an address for the subject, the fifth column, "Ph. #", list a phone number for the subject, while the sixth, seventh and eighth columns, labeled, respectively, "Curr. Name?", "Curr. Addr.?", and "Curr. Ph.?", indicate whether the name, address, and phone number fields match the search criteria. For example, if the user searched for John Smythe, and has provided an address and phone number, and the database has a John Smith who has subsequently changed his name to Jack Smythe, as shown in the table of FIG. 5, the database records will be updated as shown in the bottom row of the table of FIG. 4, and the query results returned are shown in the table of FIG. 6.

According to an embodiment of the invention, frequencies of database values can be exploited to make the comparison of search criteria and database values more efficient. Suppose that the search criteria are strings SG for given name and SL for last name. The retrieved pool of includes $(DG_1, DL_1)$, $(DG_2, DL_2)$, so on to $(DG_{10000}, DL_{10000})$. The fact is that among 10,000 strings $DG_i$ there is a much repetition. One can take advantage of that fact to speed up the overall comparison. Instead of comparing SG with each of $DG_i$, beginning from i=1, compare SG with $DG_1$, store $DG_1$, and put the result in a table. For i=2 and up, search for $DG_i$ in the table, and if found, use the result stored. If a $DG_i$ is not found, do the comparison of SG and $DG_i$ and store the result in the table.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 8:
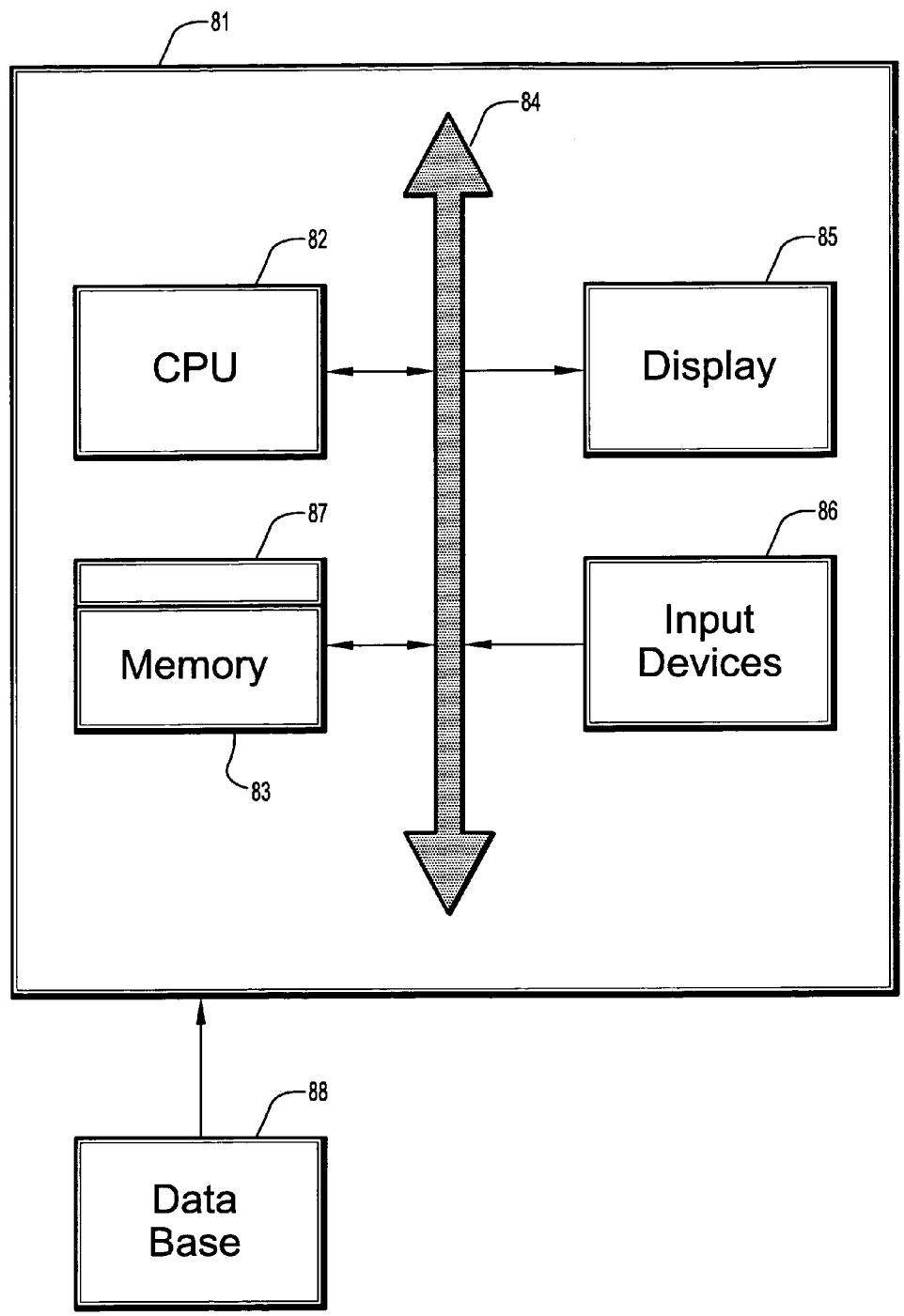
FIG. 8 is a block diagram of an exemplary computer system for implementing a data sensitive retrieval filtering process according to an embodiment of the invention.

FIG. 8 is a block diagram of an exemplary computer system for implementing data-sensitive filtering of database searches according to an embodiment of the invention. Referring now to FIG. 8, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the data from the data base 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer implemented method for data sensitive filtering in patient database searches, said method comprising the steps of:

providing a search criteria for searching a database, the search criteria comprising characters entered into multiple fields of an available plurality of search locator fields;

determining, with a processor, a retrieval formula based on said search criteria that maximizes error tolerance prior to the execution of the retrieval formula, wherein the error tolerance is maximized to achieve a candidate record range bounded by a maximum and a minimum number of records to be returned, wherein the candidate record range is achieved by establishing a probability of a subset of the characters entered into the multiple fields using a comparison of the subset of the characters to a predetermined collection of high probability character strings of said database, and wherein the error tolerance is maximized by determining a candidate record filtering condition that allows the maximum number of candidate records within the candidate record range to be retrieved within a response time requirement;

retrieving, by the processor and based on said retrieval formula, candidate records from said database, wherein the determination of the retrieval formula occurs prior to the retrieving;

scoring, by the processor, each said candidate record by comparing a search criteria locator field with a corresponding retrieved record field, wherein comparing comprises performing a field by field comparison of said locator field and said candidate record field pair to fill in components of a comparison result vector $c_j$ for a field pair j and using a field comparison method predefined for each field pair;

scoring said comparison result $c_1$ based on one or more probabilities using a formula $$score(c_j)=\log(P_{1j}(c_j))-\log(P_{0j}(c_j))=\log(P_{1j}(c_j)/P_{0j}(c_j)),$$

wherein $P_{0j}(c_j)$ and $P_{1j}(c_j)$ are probabilities that are functions of the number of matching characters in said pair of fields;

summing score($c_j$) over all fields j where the both the locator field and the corresponding field in said candidate record are not blank to calculate a first score; and determining, by the processor, whether said score of said candidate record exceeds a predefined threshold, and if said candidate score does exceed said threshold, adding said candidate record to a list of records to be returned in response to said search criteria.

2. The method of claim 1, wherein said search criteria includes a first name and a last name, and wherein the method further comprises compiling a list of names equivalent to said first name in said search criteria.

3. The method of claim 1, wherein if both a first name and a last name are specified in the search criteria, the method further comprises:
    swapping said first and last names in the search criteria;
    repeating said steps of performing a field by field comparison of the swapped locator field with the candidate record field, scoring said comparison result ci, and summing said score over all fields j to calculate a second score; and
    selecting a maximum of said first score and said second score minus a swap penalty.

4. The method of claim 3, further comprising transforming said score to a 0 to 100 scale according to a formula $$transformedScore=(score-minScore)/(maxScore-minScore)\%100,$$

wherein
    maxScore=$\Sigma_j$ maxScore$_j$,
    minScore=$\Sigma_j$ minScore$_j$,
    wherein the locator field that is used to generate the $j^{th}$ component of the comparison vector is not blank in the search criteria, and wherein maxScore$_j$=max(score($c_j$)) and minScore$_j$=mi(score($c_j$)) over all possible values of $c_j$.

5. The method of claim 1, wherein said field comparison method for a field is one of an exact distance match, a Hamming distance, an edit distance, an edit distance with swap, a first name distance, and a last name distance.

6. The method of claim 1, further comprising, for each candidate record in said list of records to be returned:
    retrieving a most recent complete record from said database for said search locator field;
    for each field that has a non-empty value in said candidate record, replacing the field value in the retrieved complete record with the corresponding value in the candidate record; and
    adding the altered complete record to said database.

7. A computer implemented method for data sensitive filtering in patient database searches, said method comprising the steps of:
    providing a search criteria for retrieving one or more records from a database comprising one or more search locator fields;
    determining, with a processor, a maximum number of candidate records to be retrieved from said database;
    determining, with the processor, a number of candidate records to be retrieved based on a number of characters in said search criteria being correct;
    determining, with the processor, a retrieval formula from said search criteria that maximizes error tolerance in said search criteria while satisfying said maximum number of candidate records, wherein the retrieval formula comprises selecting a sub-string of said search field, searching a dictionary of high frequency strings of said database for said substring, and performing a database query when said search sub-string is not found in said dictionary;
    retrieving, with the processor and based on the retrieval formula, said candidate records from said database;
    scoring, by the processor, each said candidate record by comparing a search criteria locator field with a corresponding retrieved record field, wherein comparing comprises performing a field by field comparison of said locator field and said candidate record field pair to fill in components of a comparison result vector $c_j$ for a field pair j and using a field comparison method predefined for each field pair;
    scoring said comparison result $c_j$ based on one or more probabilities using a formula $$score(c_j)=\log(P_{1j}(c_j))-\log(P_{0j}(c_j))=\log(P_{1j}(c_j)/P_{0j}(c_j)),$$

wherein $P_{0j}(c_j)$ and $P_{1j}(c_j)$ are probabilities that are functions of the number of matching characters in said pair of fields;

summing score($c_j$) over all fields j where the both the locator field and the corresponding field in said candidate record are not blank to calculate a first score; and determining, by the processor, whether said score of said candidate record exceeds a predefined threshold, and if said candidate score does exceed said threshold, adding said candidate record to a list of records to be returned in response to said search criteria.

8. The method of claim 7, wherein if a number of candidate records retrievable using said retrieval formula falls below a minimum number of candidate records, reducing said number of characters in said search criteria assumed to be correct.

9. The method of claim 7, wherein said maximum number of candidate records to be retrieved is determined from a frequency table of database values that represent probabilities of search criteria fields being included in said database, and wherein strings having probability values higher than a predefined threshold are stored in memory.

10. The method of claim 9, wherein said threshold is based on the database size, required response time, and a speed of comparison between said search criteria and said candidate records.

11. The method of claim 9, wherein said probabilities include probabilities of search criteria sub-fields being included in said database.

12. The method of claim 7, further comprising:
    comparing said search criteria with a first candidate record and storing a result of said comparison and said first candidate record in a table; and
    searching for each subsequent candidate record by searching said table, wherein if said subsequent candidate record is not found in said table, the method further comprises comparing said subsequent candidate record with said search criteria and storing said comparison result and said subsequent candidate record in said table.

13. The method of claim 7, wherein said retrieval formula comprises a logical formula formed from said one or more search locator fields.

14. The method of claim 13, wherein if said search criteria includes more than two search fields, the method further comprises forming said logical formula from a disjunction of conjunction of pairs of search criteria.

15. The method of claim 13, wherein if said search criteria includes two search fields, the method further comprises forming said logical formula from logical combinations of comparisons of the entire search fields and comparisons of partial search fields.

16. A non-transitory program storage device readable by a computer, tangibly embodying a program of instructions executable by the computer to perform method steps for data sensitive filtering in patient database searches, said method comprising the steps of:
the computer:
providing a search criteria comprising at least one string of characters entered into a plurality of search locator fields;
determining a retrieval formula from said search criteria that maximizes error tolerance in said search criteria while satisfying a candidate record range prior to the execution of the retrieval formula, wherein the error tolerance is maximized to achieve the candidate record range, and the candidate record range is achieved by establishing a probability of a subset of the characters entered into the multiple fields using a comparison of the subset of the characters to a predetermined collection of high probability character strings of said database, and wherein the error tolerance is maximized by determining a candidate record filtering condition that allows the maximum number of candidate records within the candidate record range to be retrieved within a response time requirement;
retrieving, based on the retrieval formula, candidate records from said database;
scoring each said candidate record by comparing a search criteria locator field with a corresponding retrieved record field, wherein comparing comprises performing a field by field comparison of said locator field and said candidate record field pair to fill in components of a comparison result vector $c_j$ for a field pair j and using a field comparison method predefined for each field pair;
scoring said comparison result $c_j$ based on one or more probabilities using a formula $$\text{score}(c_j) = \log(P_{1j}(c_j)) - \log(P_{0j}(c_j)) = \log(P_{1j}(c_j)/P_{0j}(c_j)),$$

wherein $P_{0j}(c_j)$ and $P_{1j}(c_j)$ are probabilities that are functions of the number of matching characters in said pair of fields; and
summing $\text{score}(c_j)$ over all fields j where the both the locator field and the corresponding field in said candidate record are not blank to calculate a first score; and determining whether said score of said candidate record exceeds a predefined threshold, and if said candidate score does exceed said threshold, adding said candidate record to a list of records to be returned in response to said search criteria.

17. The computer readable program storage device of claim 16, wherein said search criteria includes a first name and a last name, and wherein the method further comprises compiling a list of names equivalent to said first name in said search criteria.

18. The computer readable program storage device of claim 17, wherein if both a first name and a last name are specified in the search criteria, the method further comprises:
swapping said first and last names in the search criteria;
repeating said steps of performing a field by field comparison of the swapped locator field with the candidate record field, scoring said comparison result and summing said score over all fields j to calculate a second score; and
selecting a maximum of said first score and said second score minus a swap penalty.

19. The computer readable program storage device of claim 18, wherein the method further comprises transforming said score to a 0 to 100 scale according to a formula $$\text{transformedScore} = (\text{score} - \text{minScore})/(\text{maxScore} - \text{minScore})\%100,$$

wherein
$\text{maxScore} = \Sigma_j \text{maxScore}_j$,
$\text{minScore} = \Sigma_j \text{minScore}_j$,
wherein the locator field that is used to generate the $j^{th}$ component of the comparison vector is not blank in the search criteria, and wherein $\text{maxScore}_j = \max(\text{score}(c_j))$ and $\text{minScore}_j = \text{mi}(\text{score}(c_j))$ over all possible values of $c_j$.

20. The computer readable program storage device of claim 17, wherein said field comparison method for a field is one of an exact distance match, a Hamming distance, an edit distance, an edit distance with swap, a first name distance, and a last name distance.

21. The computer readable program storage device of claim 16, the method further comprising, for each candidate record in said list of records to be returned:
retrieving a most recent complete record from said database for said search locator field;
for each field that has a non-empty value in said candidate record, replacing the field value in the retrieved complete record with the corresponding value in the candidate record; and
adding the altered complete record to said database.

* * * * *